(12) United States Patent
Pyo et al.

(10) Patent No.: US 8,633,326 B2
(45) Date of Patent: Jan. 21, 2014

(54) METHOD FOR PREPARING TAXANE DERIVATIVES

(75) Inventors: Sang-Hyun Pyo, Daejeon (KR); Jin-Suk Cho, Daejeon (KR); Moon-Suk Kim, Daejeon (KR); Jai-Young Song, Daejeon (KR); Ho-Joon Choi, Daejeon (KR)

(73) Assignee: Samyang Biopharmaceuticals Corporation, Seoul (KR)

( * ) Notice: Subject to any disclaimer, the term of this patent is extended or adjusted under 35 U.S.C. 154(b) by 275 days.

(21) Appl. No.: 13/262,936

(22) PCT Filed: Dec. 3, 2009

(86) PCT No.: PCT/KR2009/007205
§ 371 (c)(1),
(2), (4) Date: Oct. 5, 2011

(87) PCT Pub. No.: WO2010/123186
PCT Pub. Date: Oct. 28, 2010

(65) Prior Publication Data
US 2012/0035379 A1 Feb. 9, 2012

(30) Foreign Application Priority Data
Apr. 24, 2009 (KR) .................. 10-2009-0036055

(51) Int. Cl.
*C07D 407/00* (2006.01)
*C07D 493/00* (2006.01)

(52) U.S. Cl.
USPC ........................................... 549/510; 549/511

(58) Field of Classification Search
USPC .................................................. 549/510, 511
See application file for complete search history.

(56) References Cited

U.S. PATENT DOCUMENTS

| 4,924,011 A | 5/1990 | Denis et al. |
| 5,939,566 A | 8/1999 | Swindell et al. |
| 6,262,281 B1 | 7/2001 | Swindell et al. |
| 2005/0101789 A1 | 5/2005 | Naidu |

FOREIGN PATENT DOCUMENTS

| EP | 1575929 A1 | 9/2005 |
| WO | WO-93/06093 A1 | 4/1993 |
| WO | WO-93/06094 A1 | 4/1993 |

OTHER PUBLICATIONS

A. Commercon et al., Tetrahedron Letters, vol. 33, 5185-5188, 1992.

*Primary Examiner* — Andrew D Kosar
*Assistant Examiner* — Raymond Covington
(74) *Attorney, Agent, or Firm* — Gifford, Krass, Sprinkle, Anderson & Citkowski, P.C.

(57) ABSTRACT

Provided is a method for preparing a taxane derivative, comprising: carrying out condensation of a phenylisoserine derivatives having a protective group introduced thereto or a mixture of isomers thereof, as a side chain, with a baccatin III derivative or 10-deacetyl-baccatin III derivative to obtain a mixture of isomers; separating the isomers via chromatography; and carrying out a reversion of the stereochemical structure of a selectively separated isomer, which is suitable for producing a taxane derivative in a large scale with high yield.

15 Claims, 8 Drawing Sheets

METHOD FOR PREPARING TAXANE DERIVATIVES

CROSS-REFERENCE TO RELATED APPLICATIONS

This application is the U.S. National Phase of PCT/KR2009/007205 filed Dec. 3, 2009, which claims priority of Korean Patent Application 10-2009-0036055 filed Apr. 24, 2009.

TECHNICAL FIELD

The present invention relates to a method for preparing a taxane derivative, and more particularly, to a method for preparing a taxane derivative comprising the steps of carrying out condensation of a phenylisoserine derivative having a protective group introduced thereto or a mixture of the derivative and its isomer, as a side chain, with a baccatin III derivative or 10-deacetyl-baccatin III derivative to obtain a mixture of isomers; separating the isomers via chromatography; and carrying out a selective reversion of the stereochemical structure of the separated isomers.

BACKGROUND ART

Taxane derivatives represented by the following Chemical Formula (I) are known as anti-cancer agents having a broad spectrum of anti-cancer effects. Among such taxane derivatives, paclitaxel or docetaxel is generally known to those skilled in the art.

(I)

In the above formula, where $R_1$ is acetyl and $R_3$ is benzoyl, the compound is paclitaxel, and where $R_1$ is hydrogen and $R_3$ is tert-butoxycarbonyl (Boc), the compound is docetaxel.

Paclitaxel, one of the taxane derivatives, is a natural substance. Thus, it can be obtained by extraction from a yew tree, or by culturing yew tree cells, followed by separation and purification. Otherwise, it can be obtained from a semi-synthesis process comprising: collecting precursors, such as baccatin III or 10-deacetyl-baccatin III, present in a relatively large amount in leaves and stems of a yew tree; and converting the precursors into paclitaxel via chemical reaction. On the other hand, docetaxel is a non-naturally occurring synthetic substance. Thus, it is obtained by a synthetic process from a suitable precursor. Like paclitaxel, docetaxel is often obtained from a semi-synthesis process using precursors, such as baccatin III or 10-deacetyl-baccatin III.

Since the taxane-based compounds were known to have excellent anti-cancer activities, many semi-synthesis processes have been developed to date in order to produce various taxane derivatives, such as paclitaxel and docetaxel.

For example, a method for preparing 10-deacetyl-baccatin III derivative (docetaxel), including carrying out condensation of an oxazolidine compound as a side chain with hydroxyl-protected 10-deacetyl-baccatin III, is known (A. Commercon et al., Tetrahedron Letters, Vol. 33, 5185-5188, 1992). However, as shown in the following reaction scheme, the method requires additional reactions, comprising converting the side chain into a cyclized oxazoline derivative, and introducing a suitable substituent to the amine group of a side chain after the condensation.

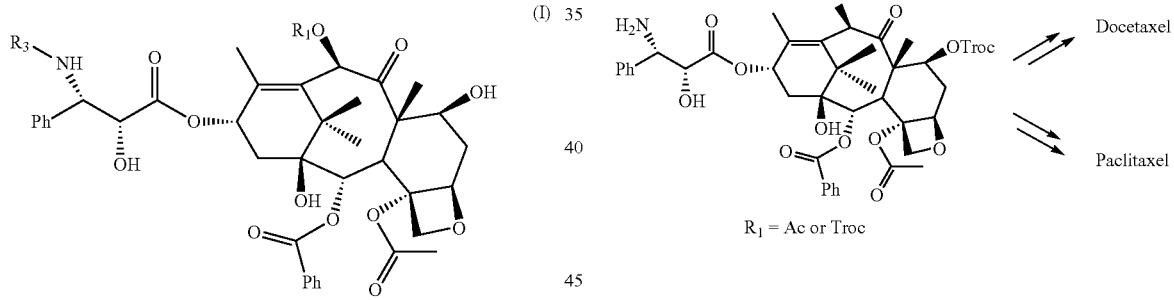

In addition, International Patent Publication No. WO93/06094 (Holton et al.) discloses a method for preparing a baccatin III derivative (paclitaxel) by carrying out condensation of a protected beta-lactam compound as a side chain with hydroxyl-protected 10-deacetyl-baccatin III. The method is useful one including a simple process. However, it requires preparation of a specific protected beta-lactam compound. Further, the condensation should be carried out at a low temperature of −45° C. or lower under an anhydrous condition, as shown in the following reaction scheme.

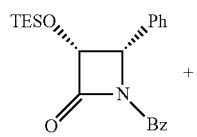

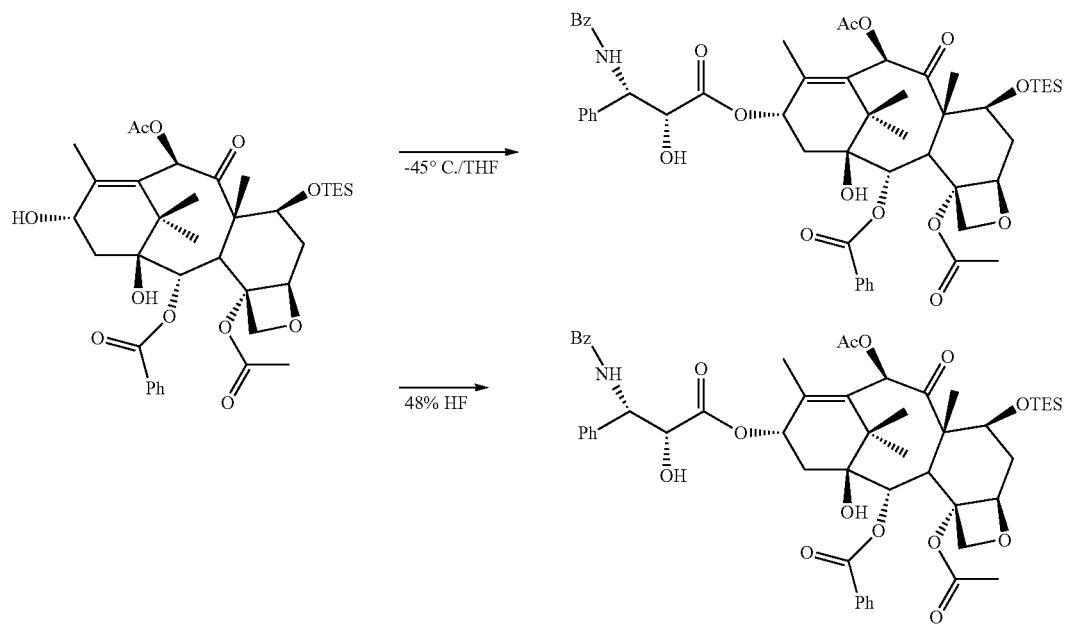

Meanwhile, U.S. Pat. No. 4,924,011 (Dennis, et al.) discloses a method for preparing a 10-deacetyl-baccatin III derivative (docetaxel) by carrying out condensation of a protected acid as a side chain with a hydroxyl-protected 10-deacetyl-baccatin III under a mild condition. However, the method inevitably produces epimers (60:40) in the process of condensation, resulting in a significant drop in yield. In addition, the 10-deacetyl-baccatin III derivative obtained after removing the protective group is present in the form of a mixture with its epimer that should be removed to a very low degree due to its cytotoxicity. However, since the physicochemical properties of the epimer are similar to those of the derivative, there is a difficulty in separating the epimer from the mixture in an industrial scale.

DISCLOSURE OF INVENTION

Technical Problem

Therefore, the present invention has been made in an effort to solve the above-described problems associated with the related art. It is an object of the present invention to provide a method for preparing a desired taxane derivative with high yield by carrying out condensation of baccatin III or 10-deacetyl-baccatin III derivative with a protected phenylisoserine derivative or a mixture with its isomers as a side chain to obtain a mixture of isomers; separating epimers effectively from the mixture via chromatography in a predetermined step; and carrying out a selective reversion of the stereochemical structure of a separated epimer.

Solution to Problem

In one aspect, the present invention provides a method (1) for preparing a taxane derivative, comprising the steps of:
1) carrying out condensation of a side chain with baccatin III or 10-deacetyl-baccatin III derivative having protective group(s) introduced to 7-hydroxyl group and/or 10-hydroxyl group, represented by the following Chemical Formula III, to obtain a mixture (IVa, IVb) of a compound represented by the following Chemical Formula IVa and a compound represented by the following Chemical Formula IVb, wherein the side chain is selected from a (2R,3S)-phenylisoserine derivative, represented by the following Chemical Formula IIa and having protected groups introduced to 2-hydroxyl group and 3-amino group and a mixture of the (2R,3S)-phenylisoserine derivative with its isomer, a (2S,3S)-phenylisoserine derivative represented by the following Chemical Formula IIb;

-continued

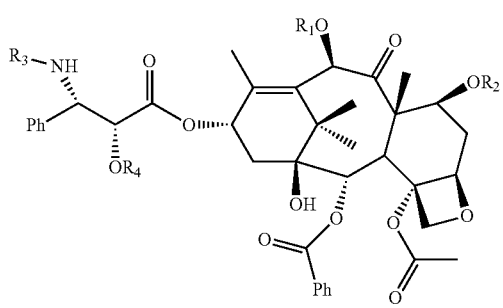

IVa

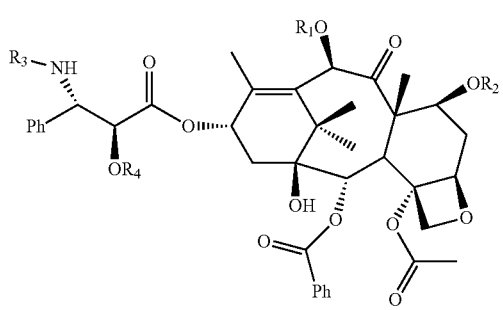

IVb 2) deprotecting the side chain of the mixture (IVa, IVb) obtained from step 1) to remove the protective group at C-2 position thereof and then obtain a mixture (Va, Vb) of a compound represented by the following Chemical Formula Va with a compound represented by the following Chemical Formula Vb;

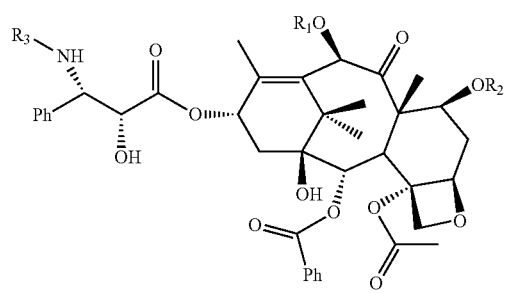

Va

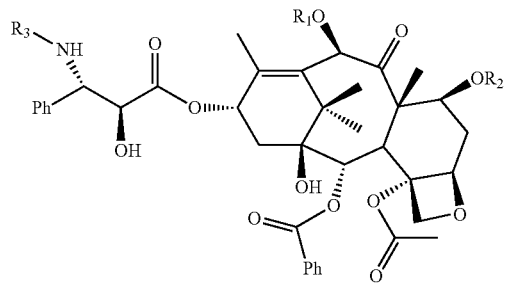

Vb 3) separating the mixture (Va, Vb) obtained from step 2) via chromatography to obtain each isomer compound (Va) and (Vb);

4) carrying out a stereochemical reversion of one isomer compound (Vb) in the compounds obtained from step 3) into the other isomer compound (Va); and 5) deprotecting the isomer compound (Va) obtained from steps 3) and 4) to remove the protective group(s) at C-7 and/or C-10 position thereof and then obtain a taxane derivative represented by the following Chemical Formula I:

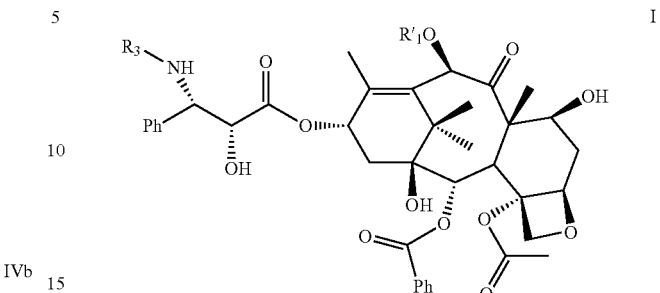

I wherein $R_1$ and $R_2$ are independently acetyl (Ac), tert-butyldimethylsilyl (TBS), triethylsilyl (TES), ethoxyethyl (EE), or 2,2,2-trichloroethoxycarbonyl (Troc);

$R_3$ is benzoyl (Bz) or tert-butoxycarbonyl (Boc);

$R_4$ is Ac, TBS, TES, EE, or Troc;

$R_1'$ is Ac or H; and

Ph is phenyl.

In another aspect, the present invention provides a method (2) for preparing a taxane derivative, comprising the steps of:

1) carrying out condensation of a side chain with baccatin III or 10-deacetyl-baccatin III derivative having protective group(s) introduced to 7-hydroxyl group and/or 10-hydroxyl group, represented by Chemical Formula III, to obtain a mixture (IVa, IVb) of a compound represented by Chemical Formula IVa and a compound represented by Chemical Formula IVb, wherein the side chain is selected from a (2R,3S)-phenylisoserine derivative, represented by Chemical Formula IIa and having protected groups introduced to 2-hydroxyl group and 3-amino group and a mixture of the (2R,3S)-phenylisoserine derivative with its isomer, a (2S,3S)-phenylisoserine derivative represented by Chemical Formula IIb;

2) separating the mixture (IVa, IVb) obtained from step 1) via chromatography to obtain each isomer compound (IVa) and (IVb);

3) deprotecting the side chain of each isomer compound (IVa) and (IVb) obtained from step 2) to remove the protective group at C-2 position thereof and then obtain a compound represented by Chemical Formula Va and a compound represented by Chemical Formula Vb;

4) carrying out a stereochemical reversion of one isomer compound (Vb) in the compounds obtained from step 3) into the other isomer compound (Va); and 5) deprotecting the isomer compound (Va) obtained from steps 3) and 4) to remove the protective group(s) at C-7 and/or C-10 position thereof and then obtain a taxane derivative represented by Chemical Formula I.

In still another aspect, the present invention provides a method (3) for preparing a taxane derivative, comprising the steps of:

1) carrying out condensation of a side chain with baccatin III or 10-deacetyl-baccatin III derivative having protective group(s) introduced to 7-hydroxyl group and/or 10-hydroxyl group, represented by Chemical Formula III, to obtain a mixture (IVa, IVb) of a compound represented by Chemical Formula IVa and a compound represented by Chemical Formula IVb, wherein the side chain is selected from a (2R,3S)-phenylisoserine derivative, represented by Chemical Formula IIa and having protected groups introduced to 2-hydroxyl group and 3-amino group and a mixture of the (2R,3S)-phenylisoserine derivative with its isomer, a (2S,3S)-phenylisoserine derivative represented by Chemical Formula IIb;

2) deprotecting the mixture (IVa, IVb) obtained from step 1) to remove the protective group(s) at C-7 and/or C-10 position thereof and then obtain a mixture (VIa, VIb) of a compound represented by the following Chemical Formula VIa with a compound represented by the following Chemical Formula VIb;

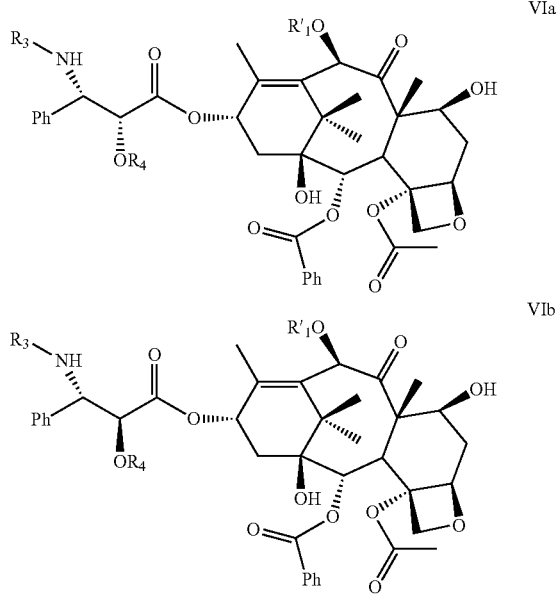

(wherein $R_1'$, $R_3$, $R_4$ and Ph are the same as defined above.)

3) separating the mixture (VIa, VIb) obtained from step 2) via chromatography to obtain each isomer compound (VIa) and (VIb);

4) deprotecting the side chain of each isomer compound obtained from step 3) to remove the protective group at C-2 position thereof; and 5) carrying out a stereochemical reversion of one isomer compound having a (2S,3S)-side chain in the compounds obtained from step 4) into the other isomer compound having a (2R,3S)-side chain to obtain a taxane derivative represented by Chemical Formula I.

Advantageous Effects of Invention

According to one aspect of the present invention, a phenylisoserine derivative or a mixture with its isomer is used as a side chain to be condensed with baccatin III or 10-deacetyl-baccatin III derivative, thereby providing a mixture of isomers. Then, each isomer is separated from the mixture via chromatography, and a selective reversion of one isomer is performed to produce a taxane derivative with high efficiency. Therefore, it is possible to use each chiral isomer as well as a mixture of isomers as a side chain phenylisoserine derivative, and thus to reduce the cost needed for producing the side chain significantly. It is also possible to separate the isomers produced during the reaction effectively by using a simple chromatography process amenable to large-scale separation. As a result, the method according to the present invention is suitable for producing a taxane derivative in a large scale with high yield.

BRIEF DESCRIPTION OF DRAWINGS

The present invention will now be described in detail with reference to certain example embodiments thereof illustrated in the accompanying drawings which are given hereinbelow by way of illustration only, and thus are not limitative of the present invention, and wherein.

BEST MODE FOR CARRYING OUT THE INVENTION

Figure 1:
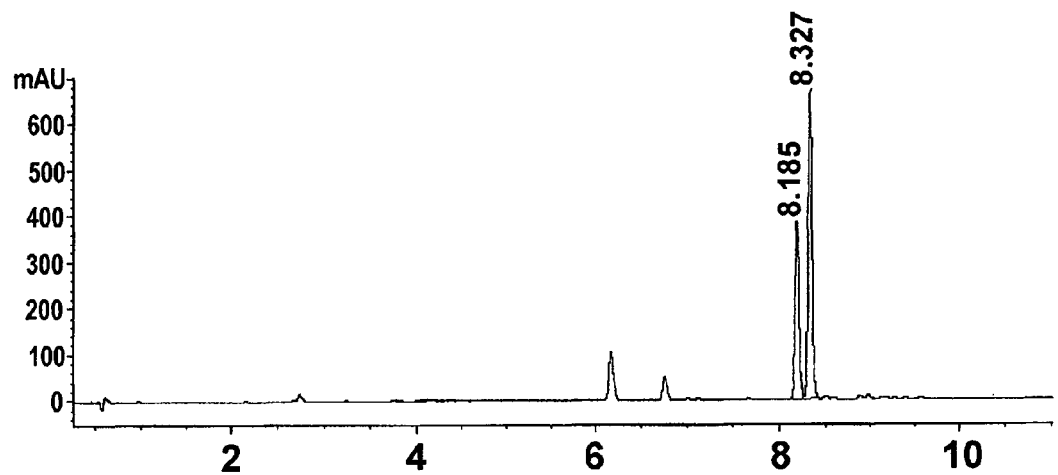
FIG. 1 is an analytical HPLC chromatogram of the mixture of (2'R,3'S)-2'-Ac-7,10-di-Troc-docetaxel (IVa) with (2'S,3'S)-2'-Ac-7,10-di-Troc-docetaxel (IVb) obtained in accordance with Example 1.

Hereinafter, a reference will now be made in detail to various embodiments of the present invention, examples of which are illustrated in the accompanying drawings and described below. While the invention will be described in conjunction with example embodiments, it will be understood that the present description is not intended to limit the invention to those example embodiments. On the contrary, the invention is intended to cover not only the example embodiments, but also various alternatives, modifications, equivalents and other embodiments, which may be included within the spirit and scope of the invention as defined by the appended claims.

According to one embodiment of the present invention, there is provided a method (1) for preparing a taxane derivative, comprising the steps of:

1) carrying out condensation of a side chain with baccatin III or 10-deacetyl-baccatin III derivative having protective group(s) introduced to 7-hydroxyl group and/or 10-hydroxyl group, represented by Chemical Formula III, to obtain a mixture (IVa, IVb) of a compound represented by Chemical Formula IVa and a compound represented by Chemical Formula IVb, wherein the side chain is selected from a (2R,3S)-phenylisoserine derivative, represented by Chemical Formula IIa and having protected groups introduced to 2-hydroxyl group and 3-amino group and a mixture of the (2R,3S)-phenylisoserine derivative with its isomer, a (2S,3S)-phenylisoserine derivative represented by Chemical Formula IIb;

2) deprotecting the side chain of the mixture (IVa, IVb) obtained from step 1) to remove the protective group at C-2 position thereof and then obtain a mixture (Va, Vb) of a compound represented by Chemical Formula Va with a compound represented by Chemical Formula Vb;

3) separating the mixture (Va, Vb) obtained from step 2) via chromatography to obtain each isomer compound (Va) and (Vb);

4) carrying out a stereochemical reversion of one isomer compound (Vb) in the compounds obtained from step 3) into the other isomer compound (Va); and 5) deprotecting the isomer compound (Va) obtained from steps 3) and 4) to remove the protective group(s) at C-7 and/or C-10 position thereof and then obtain a taxane derivative represented by Chemical Formula I.

Hereinafter, each step for preparing a taxane derivative will be explained in more detail.

In step 1), (2R,3S)-phenylisoserine derivative or (2S,3S)-phenylisoserine derivative, having protective groups introduced to 2-hydroxyl group and 3-amino group, is used as a side chain. In the phenylisoserine derivative, 2-hydroxyl group is protected with a protective group, such as acetyl (Ac), tert-butyldimethylsilyl (TBS), triethylsilyl (TES), ethoxyethyl (EE) or 2,2,2-trichloroethoxycarbonyl (Troc), while 3-amino group is protected with a protective group, such as benzoyl (Bz) or tert-butoxycarbonyl (Boc). In general, each individual isomer, i.e., (2R,3S)-phenylisoserine or (2S,3S)-phenylisoserine derivative, C-2 carbon atom of which is pure chiral, is used. However, since a mixture of the chiral isomers (IIa, IIb) as well as each chiral isomer may be used in the present invention without further separation, it is possible to reduce the cost needed for producing the side chain significantly.

Baccatin III or 10-deacetyl-baccatin III derivative used in step 1) as a starting material is protected with protective groups ($R_1$, $R_2$) selected from Ac, TBS, TES, EE and Troc, independently at C-7 and C-10 hydroxyl groups.

In step 1), the side chain compound (IIa, IIb) is condensed with baccatin III or 10-deacetyl-baccatin III derivative (III) in the presence of a suitable solvent at 0-100° C. by adding a condensing agent and dehydrating agent thereto. Particular examples of the solvent include anhydrous organic solvents, such as anhydrous toluene, benzene and xylene, and those of the condensing agent include carbodiimides, such as dicyclohexylcarbodiimide (DCC), and reactive carbonates, such as di-2-pyridyl carbonate. Particular examples of the dehydrating agent include dialkylaminopyridines, such as 4-dimethylaminopyridine (DMAP). Each of the side chain, the condensing agent and the dehydrating agent is used in an amount of 0.1-10 mols based on baccatin III or 10-deacetyl-baccatin III derivative (III).

In step 2), the mixture of the isomers (IVa, IVb) obtained from step 1) is deprotected at C-2 position of the side chain thereof. For this, a deprotecting agent, such as an acid (e.g. HCl), hydrogen peroxide solution or saturated sodium carbonate, is added in the presence of a suitable solvent selected from lower alcohols, halogenated alkanes, toluene and tetrahydrofuran (THF), and the resultant mixture is agitated at low temperature or room temperature to obtain a mixture of the compound represented by Chemical Formula Va with the compound represented by Chemical Formula Vb. A suitable solvent, deprotecting agent and reaction conditions may be selected from various deprotecting methods known to those skilled in the art depending on the particular type of the protective group. For example, when the protective groups, $R_1$ and $R_2$ are independently Troc and the protective group at C-2 position of the side chain is Ac, aqueous saturated sodium carbonate solution and hydrogen peroxide are added in the presence of an organic solvent, such as tetrahydrofuran (THF), under agitation to remove the protective group at C-2 position of the side chain. In addition, when the protective group at C-2 position of the side chain is TBS, diluted HCl is added in the presence of anhydrous ethanol, and the resultant mixture is agitated and neutralized with saturated sodium carbonate to remove the protective group at C-2 position of the side chain.

In step 3), the mixture of isomers (Va, Vb) obtained from step 2) is separated via chromatography to obtain each individual isomer compound. Herein, the chromatography-based separation is carried out in a normal phase chromatography mode using a column packed with silica gel with ease in an industrial scale. In general, silica gel particles having a diameter of 5 μm are used in order to separate a small amount of useful substance. However, according to one embodiment of the present invention, silica gel particles having a particle diameter of 5-120 μm, preferably 20-60 μm are used, and thus a scale-up for mass production is allowed and high cost-efficiency is realized. Particular examples of a mobile phase that may be used include a solvent selected from dichloromethane, chloroform, ethyl acetate, hexane and pentane, or a mixture thereof with another solvent selected from alcohols (e.g. methanol) and acetonitrile. Such a chromatography-based separation process allows easy separation of the mixture of isomers (Va, Vb) into each individual isomer, and is amenable to injection of a large amount of the mixture, thereby realizing high industrial applicability. If the separation step, i.e., step 3) is omitted from the method according to the present invention, a mixture of docetaxel with epi-docetaxel is obtained. It is very difficult to separate the mixture, and thus such a variant method is not commercially applicable.

In step 4), the isomer compound represented by Chemical Formula (Vb) in the isomer compounds obtained from step 3) is reversed stereochemically into the compound represented by Chemical Formula (Va). Step 4) is carried out by adding triphenylphosphine (PPh3), diethylazodicarboxylate (DEAD) and 4-nitrobenzoic acid to the compound (Vb) separated as described above in the presence of an organic solvent, such as dichloromethane, tetrahydrofuran (THF), methanol or diethyl ether, in order to reverse its stereochemical structure into the compound (Va). This reaction is useful for the stereochemical reversion of a hydroxyl group. In addition, diethylazodi-carboxylate may be replaced by di-tert-butylazodicarboxylate. Triphenylphosphine, di-ethylazodicarboxylate and 4-nitrobenzoic acid are used in an amount of 0.1-10 mols.

In step 5), the compound (Va) separated from step 3) is mixed with the compound (Va) obtained from the reversion in step 4), and the resultant compound is deprotected at C-7 and/or C-10 position thereof to provide a taxane derivative represented by Chemical Formula (I). To carry out the deprotection in step 5), a deprotecting agent, such as an acid or metal catalyst, is added in the presence of a suitable solvent selected from alcohols, halogenated alkanes, toluene and tetrahydrofuran (THF), and the resultant mixture is agitated at low temperature or room temperature. A suitable solvent, deprotecting agent and reaction conditions may be selected from various deprotecting methods known to those skilled in the art depending on the particular type of the protective group. For example, when the protective group is Troc, acetic acid, distilled water and zinc are added in the presence of methanol, and deprotection is performed under heating and agitation. When the protective group is TES, diluted HCl is added in the presence of methanol as a solvent at low temperature, and the resultant mixture is heated gradually to room temperature under agitation. As an alternative deprotecting method for TES, 40-50% hydrofluoric acid (HF), preferably HCl is added in the presence of pyridine, followed by agitation.

A partial modification in the procedure of each step is also included in the present invention. However, it is preferred that the method is carried out in the orderly manner as described above.

In brief, a particular embodiment of the method (1) for preparing a taxane derivative is represented by the following Reaction Scheme 1:

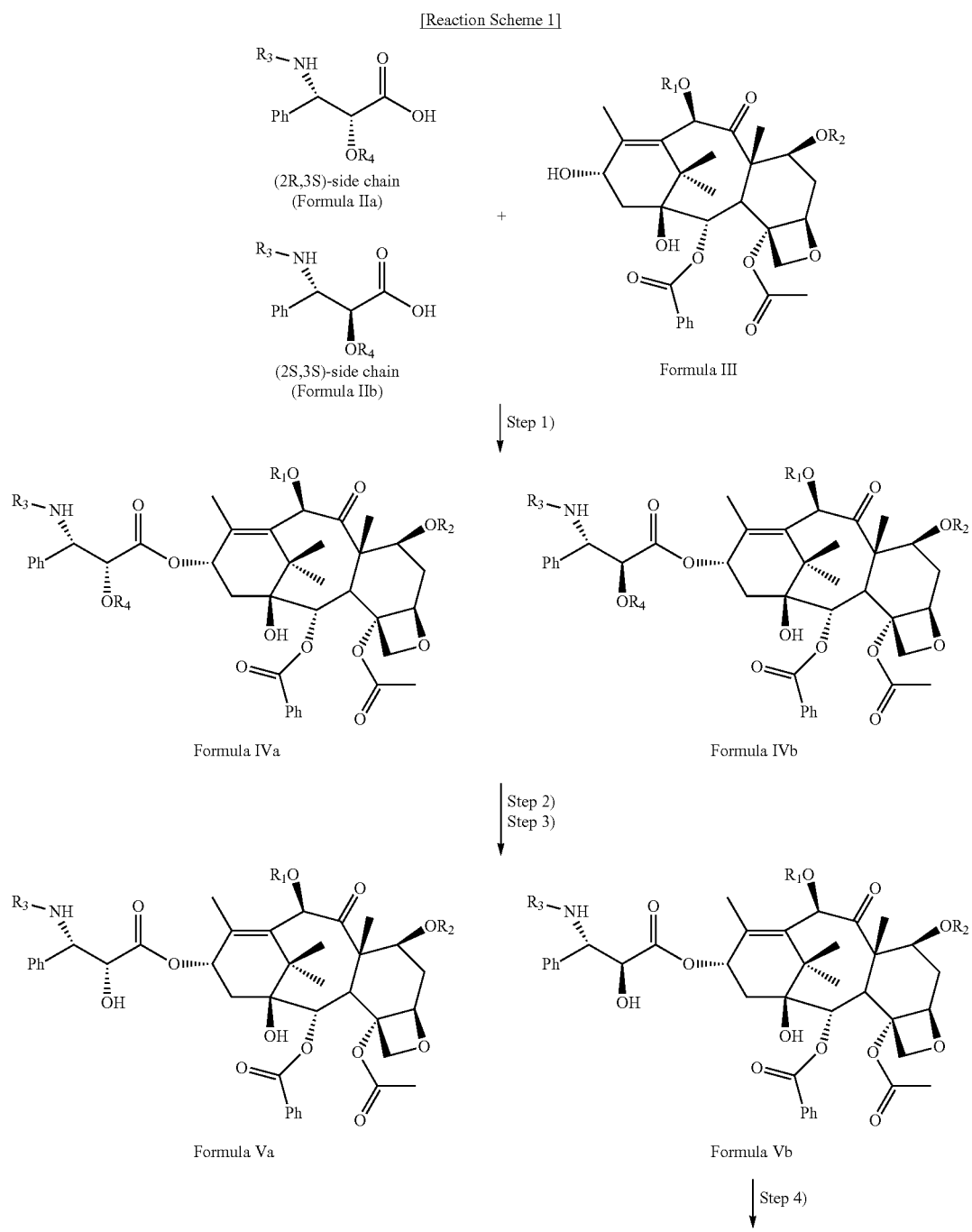

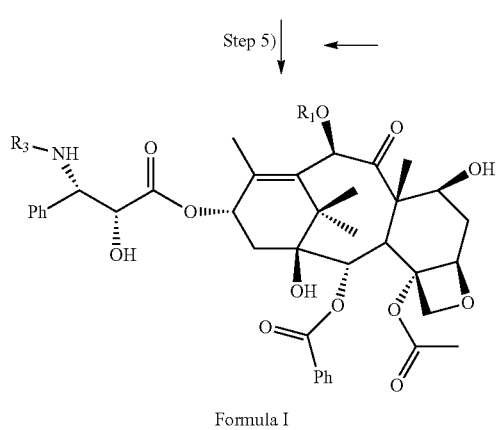

Formula I

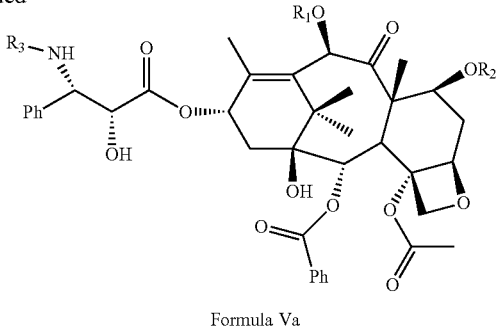

Formula Va

In the above Reaction Scheme 1, $R_1$ and $R_2$ are independently acetyl (Ac), tert-butyldimethylsilyl (TBS), triethylsilyl (TES), ethoxyethyl (EE), or 2,2,2-trichloroethoxycarbonyl (Troc);

$R_3$ is benzoyl (Bz) or tert-butoxycarbonyl (Boc);

$R_4$ is Ac, TBS, TES, EE, or Troc;

$R_1'$ is Ac or H; and

Ph is phenyl.

According to another embodiment of the present invention, step 2) and step 3) in the above method (1) reverse the order relative to each other. Thus, there is provided a method (2) for preparing a taxane derivative, comprising the steps of:

1) carrying out condensation of a side chain with baccatin III or 10-deacetyl-baccatin III derivative having protective group(s) introduced to 7-hydroxyl group and/or 10-hydroxyl group, represented by Chemical Formula III, to obtain a mixture (IVa, IVb) of a compound represented by Chemical Formula IVa and a compound represented by Chemical Formula IVb, wherein the side chain is selected from a (2R,3S)-phenylisoserine derivative, represented by Chemical Formula IIa and having protected groups introduced to 2-hydroxyl group and 3-amino group and a mixture of the (2R,3S)-phenylisoserine derivative with its isomer, a (2S,3S)-phenylisoserine derivative represented by Chemical Formula IIb;

2) separating the mixture (IVa, IVb) obtained from step 1) via chromatography to obtain each isomer compound (IVa) and (IVb);

3) deprotecting the side chain of each isomer compound obtained from step 2) to remove the protective group at C-2 position thereof and then obtain a compound represented by Chemical Formula Va and a compound represented by Chemical Formula Vb;

4) carrying out a stereochemical reversion of one isomer compound (Vb) in the compounds obtained from step 3) into the other isomer compound (Va); and 5) deprotecting the isomer compound (Va) obtained from steps 3) and 4) to remove the protective group(s) at C-7 and/or C-10 position thereof and then obtain a taxane derivative represented by Chemical Formula (I).

According to still another embodiment of the present invention, the compounds obtained from step 1) in the above method (2) are deprotected at C-7 and/or C-10 positions thereof, and then steps 2)-4) are carried out sequentially. Thus there is provided a method (3) for preparing a taxane derivative comprising the steps of:

1) carrying out condensation of a side chain with baccatin III or 10-deacetyl-baccatin III derivative having protective group(s) introduced to 7-hydroxyl group and/or 10-hydroxyl group, represented by Chemical Formula III, to obtain a mixture (IVa, IVb) of a compound represented by Chemical Formula IVa and a compound represented by Chemical Formula IVb, wherein the side chain is selected from a (2R,3S)-phenylisoserine derivative, represented by Chemical Formula IIa and having protected groups introduced to 2-hydroxyl group and 3-amino group and a mixture of the (2R,3S)-phenylisoserine derivative with its isomer, a (2S,3S)-phenylisoserine derivative represented by Chemical Formula IIb;

2) deprotecting the mixture (IVa, IVb) obtained from step 1) to remove the protective group(s) at C-7 and/or C-10 position thereof and then obtain a mixture (VIa, VIb) of a compound represented by Chemical Formula VIa with a compound represented by Chemical Formula VIb;

3) separating the mixture (VIa, VIb) obtained from step 2) via chromatography to obtain each isomer compound (VIa) and (VIb);

4) deprotecting the side chain of each isomer compound obtained from step 3) to remove the protective group at C-2 position thereof; and 5) carrying out a stereochemical reversion of one isomer compound having a (2S,3S)-side chain in the compounds obtained from step 4) into the other isomer compound having a (2R,3S)-side chain to obtain a taxane derivative represented by Chemical Formula (I).

In the above-mentioned methods (2) and (3), each step is carried out under the same conditions as described hereinabove with reference to method (1).

The taxane derivative obtained by the method according to various embodiments of the present invention includes docetaxel, paclitaxel or analogs thereof, preferably docetaxel.

MODE FOR THE INVENTION

Hereinafter, the present invention will be explained in more detail with reference to the examples. The following examples are for illustrative purposes only and not intended to limit the scope of the present invention.

The purity and yield of each product obtained from the following Examples is determined quantitatively by using HPLC under the conditions as described in the following Table 1:

TABLE 1

| | |
|---|---|
| Instrument | Agilent Technology 1200 Series HPLC |
| Column | Imtakt, C18 4.6 × 75 mm, 3 micron |
| Column temperature | 35° C. |
| Mobile phase | Acetonitrile: water (50-90% concentration gradient) |
| Flow rate | 1.5 ml/min |
| Injection amount | 3 μl |
| Detector | UV (227 nm) |

In the following Example 1, used are a side chain, whose hydroxyl group is protected with Ac, and 10-deacetyl-baccatin III derivative protected with Troc.

EXAMPLE 1

Step 1): Condensation of (2R,3S)-2-Ac-N-Boc-3-phenylisoserine (Chemical Formula IIa) with 7,10-di-Troc-10-deacetyl-baccatin III (Chemical Formula III)

First, 1 g of 7,10-di-Troc-10-deacetyl-baccatin III (III) and 0.7 g of (2R,3S)-2-Ac-N-Boc-3-phenylisoserine (IIa) are dissolved into 10 mL of dry toluene, and an equimolar amount of DMAP is added thereto. Next, a solution of an equimolar amount of DCC dissolved in 5 mL of dry toluene is added dropwise thereto and the reaction mixture is heated to 50° C. under agitation to perform a reaction. After the completion of the reaction, 10 mL of distilled water is added to quench the reaction, and the reaction mixture is agitated for 1 hour at room temperature. Then, the reaction mixture is filtered. The filtrate is concentrated and dried, and then subjected to chromatography through a silica gel column using 5% metanol/95% dichloromethane as a mobile phase, followed by concentration and drying, to obtain 1.2 g of a mixed dry solid of (2'R,3'S)-2'Ac-7,10-di-Troc-docetaxel (Chemical Formula IVa) and (2'S,3'S)-2'-Ac-7,10-di-Troc-docetaxel (Chemical Formula IVb), which, in turn is determined by HPLC (see FIG. 1).

EXAMPLE 2

Figure 2:
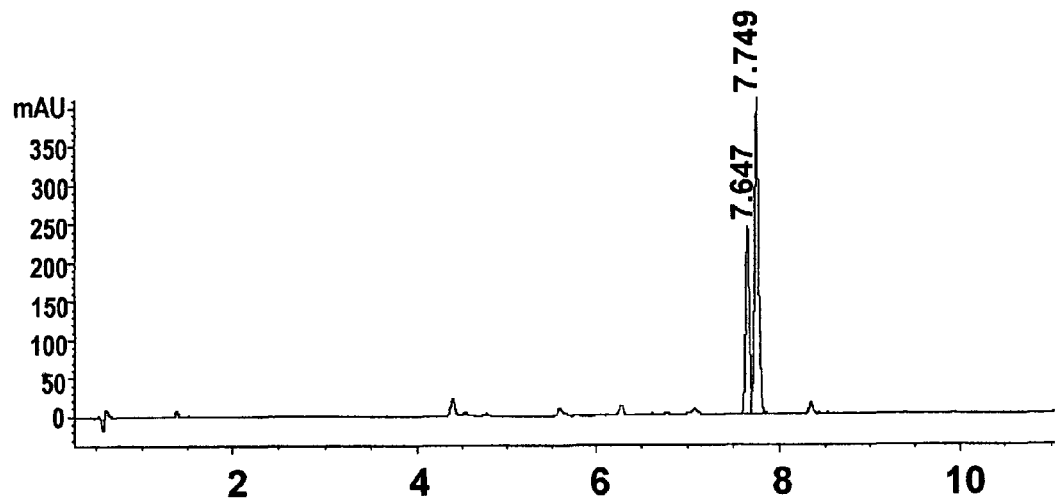
FIG. 2 is an analytical HPLC chromatogram of the mixture of (2'R,3'S)-7,10-di-Troc-docetaxel (Va) with (2'S,3'S)-7,10-di-Troc-docetaxel (Vb) obtained in accordance with Example 2.

Step 2): Deprotection of Mixture of (2'R,3'S)-2'-Ac-7,10-di-Troc-docetaxel (IVa) and (2'S,3'S)-2'-Ac-7,10-di-Troc-docetaxel (IVb) at 2'-Ac Group First, 1 g of the dry sold obtained from Example 1 is dissolved into 10 mL of THF, and 2 mL of aqueous saturated sodium carbonate solution and 2 mL of hydrogen peroxide solution (30%) are added thereto. While adding aqueous saturated sodium carbonate solution and hydrogen peroxide solution, each 0.5 mL, dropwise thereto under agitation at room temperature, the reaction is monitored by HPLC. After the starting materials are consumed completely, the reaction mixture is neutralized with 0.1N HCl and extracted with ethyl acetate. The extract is washed successively with aqueous saturated sodium carbonate solution, distilled water and saline, and then is concentrated and dried to obtain 8.5 g of a mixed dry solid of (2'R,3'S)-7,10-di-Troc-docetaxel (Chemical Formula Va) and (2'S,3'S)-7,10-di-Troc-docetaxel (Chemical Formula Vb), which, in turn, is determined by HPLC (see FIG. 2).

EXAMPLE 3

Figure 3:
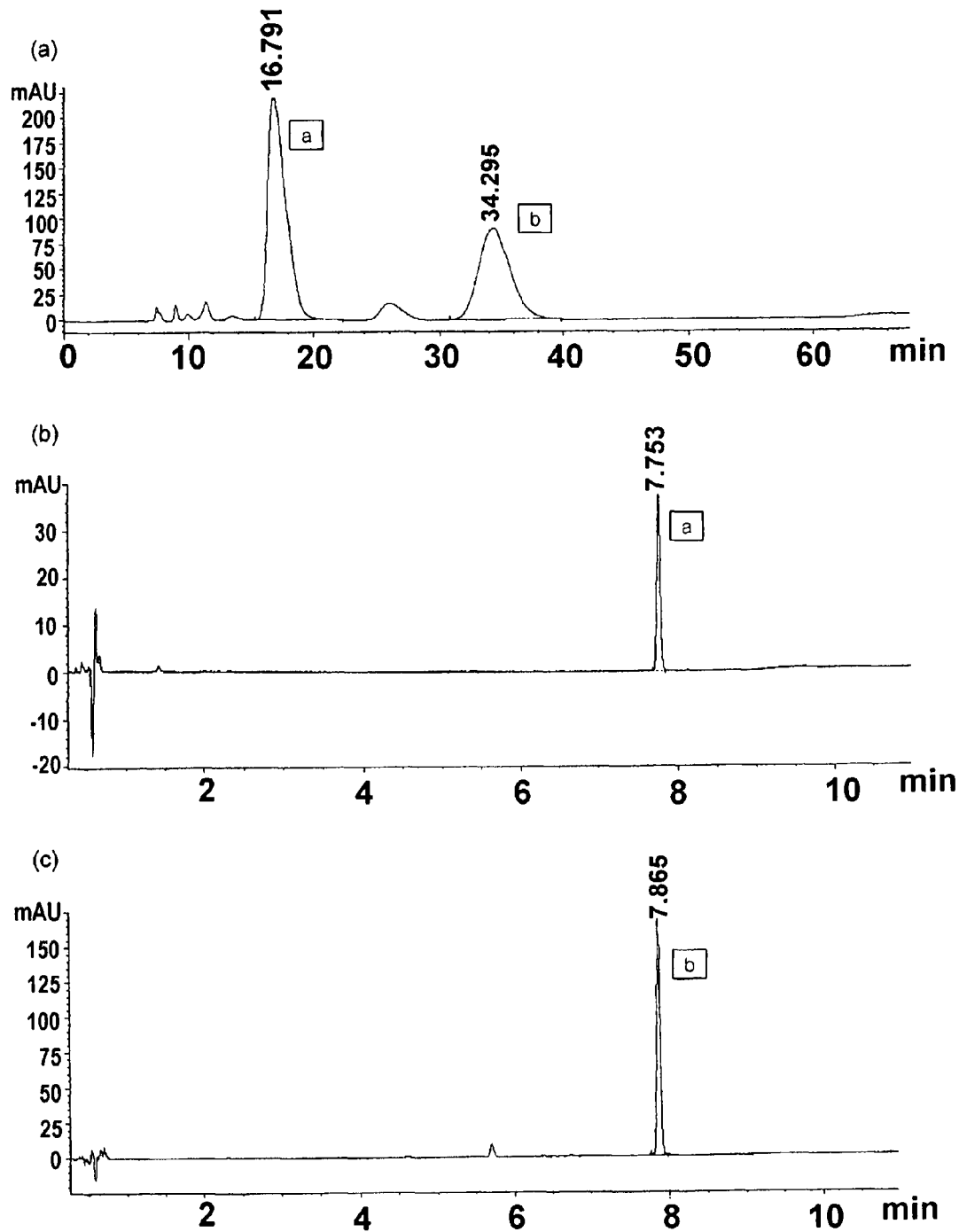
FIGS. 3a-3c are chromatograms for the separation of the mixture of (2'R,3'S)-7,10-di-Troc-docetaxel (Va) with (2'S,3'S)-7,10-di-Troc-docetaxel (Vb) obtained in accordance with Example 3, an analytical HPLC chromatogram of (2'R,3'S)-7,10-di-Troc-docetaxel (Va), and an analytical HPLC chromatogram of (2'S,3'S)-7,10-di-Troc-docetaxel (Vb), respectively.

Step 3): Separation of Mixture of (2'R,3'S)-7,10-di-Troc-docetaxel (Va) and (2'S,3'S)-7,10-di-Troc-docetaxel (Vb) into Each Isomer The mixed dry solid obtained from Example 2 is subjected to liquid chromatography with a column (0.45×90 cm) packed with silica gel (20 μm) in a scale-down mode to determine the separation efficiency. A mobile phase, 0.5% methanol/99.5% dichloromethane solution, is used at a flow rate of 1.5 mL/min to equilibrate the chromatography condition, and 4 mg of the sample is dissolved into the mobile phase solvent. All of sample is loaded onto the column. While the column is eluted continuously with the mobile phase solvent, the chromatogram is obtained by using a UV detector (FIG. 3a). The peaks corresponding to each of the isomers are collected and determined by HPLC (FIGS. 3b and 3c).

EXAMPLE 3-1

Step 3): Separation of Mixture of (2'R,3'S)-7,10-di-Troc-docetaxel (Va) and (2'S,3'S)-7,10-di-Troc-docetaxel (Vb) into Each Isomer (Scale-Up)

Figure 4:
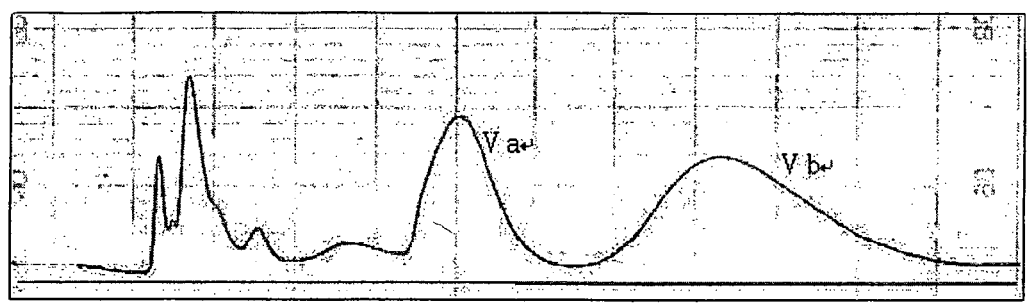
FIG. 4 is a chromatogram for the separation of the mixture of (2'R,3'S)-7,10-di-Troc-docetaxel (Va) with (2'S,3'S)-7,10-di-Troc-docetaxel (Vb) obtained in accordance with Example 3-1.

The mixed dry solid obtained from Example 2 is subjected to liquid chromatography with a column (1.5×90 cm) packed with silica gel (60-100 μm, Timely, Japan) in a scale-up mode to determine the separation efficiency. A mobile phase, 0.5% methanol/99.5% dichloromethane solution, is used at a flow rate of 20 mL/min to equilibrate the chromatography condition, and 500 mg of the sample is dissolved into the mobile phase solvent. All of sample is loaded onto the column. While the column is eluted continuously with the mobile phase solvent, the chromatogram is obtained by using a UV detector (FIG. 4). The peaks corresponding to each of the isomers are collected to obtain 165 mg of (2'R,3'S)-7,10-di-Troc-docetaxel (Va) and 220 mg of (2'S,3'S)-7,10-di-Troc-docetaxel (Vb). This example demonstrates that the separation process is amenable to scale-up.

EXAMPLE 4

Step 4): Reversion of (2'S,3'S)-7,10-di-Troc-docetaxel (Vb) into (2'R,3'S)-7,10-di-Troc-docetaxel (Va)

Figure 5:
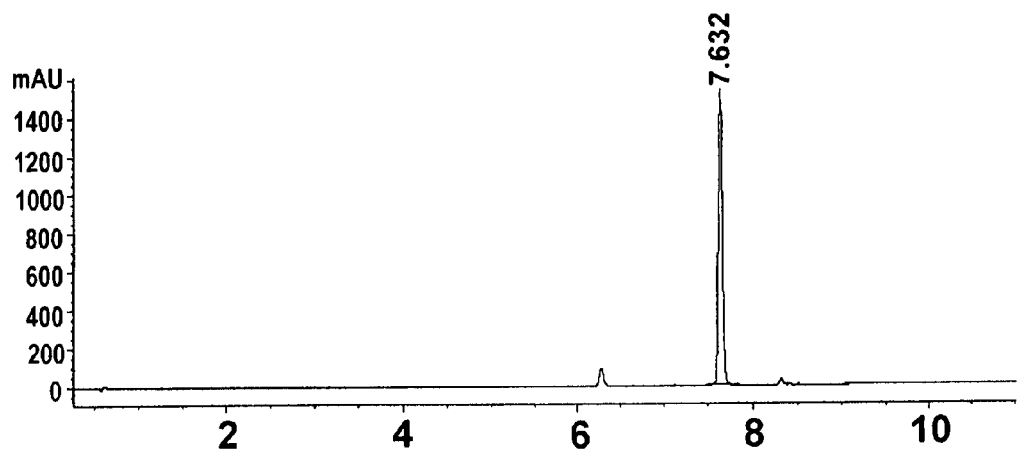
FIG. 5 is an analytical HPLC chromatogram of (2'R,3'S)-7,10-di-Troc-docetaxel (Va) converted in accordance with Example 4.

First, 20 mg of (2'S,3'S)-7,10-di-Troc-docetaxel (Vb) separated from Example 3 is dissolved into 2 mL of THF, and 20 mg of triphenylphosphine dissolved in 2 mL of THF, 20 mg of diethylazodicarboxylate and 10 mg of 4-nitrobenzoic acid are added dropwise thereto to perform a reaction under agitation. The reaction mixture is extracted by adding distilled water, the resultant product is dried and dissolved in THF, and then potassium hydroxide (KOH) is added thereto to recover a target product, (2'R,3'S)-7,10-di-Troc-docetaxel (Va), which, in turn, is determined by HPLC (FIG. 5).

EXAMPLE 5

Step 5): Deprotection of (2'R,3'S)-7,10-di-Troc-docetaxel (Va) at Troc Group

Figure 6:
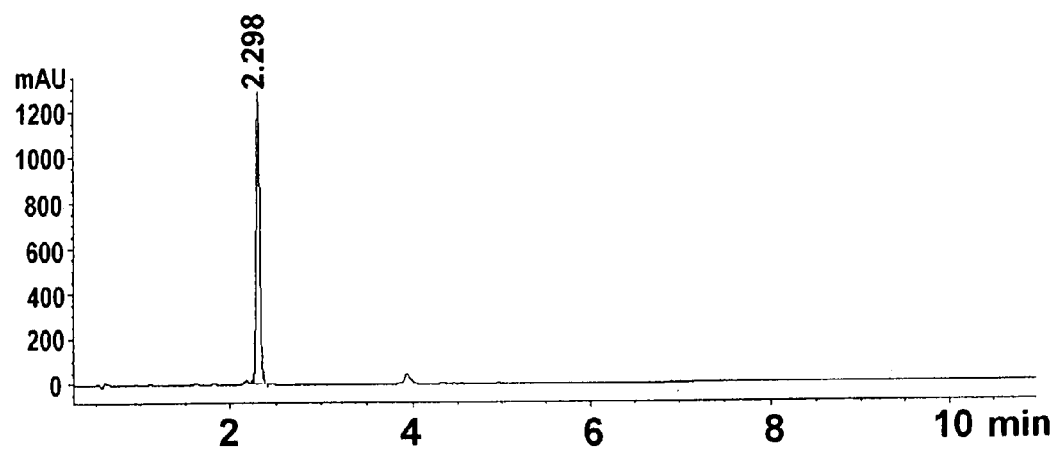
FIG. 6 is an analytical HPLC chromatogram of 10-deacetyl-baccatin III derivative obtained in accordance with Example 5.

First, 0.1 g of (2'R,3'S)-7,10-di-Troc-docetaxel (Va) obtained from Examples 3 and 4 is dissolved in a mixed solvent of 1 mL of methanol and 1 mL of acetic acid. Next, 0.1 g of zinc powder washed with 5% HCl is added thereto to perform a reaction under agitation at 60° C. After the reaction materials are consumed, 5 mL of distilled water is added thereto to form precipitate, which, in turn, is filtered to obtain a dry solid. The dry solid is dissolved into ethyl acetate, washed with aqueous saturated sodium carbonate, distilled water and saline, and concentrated and dried to obtain 0.072 g of a dry sold, 10-deacetyl-baccatin III derivative (docetaxel). The dry solid is determined by HPLC (FIG. 6).

EXAMPLE 6

Figure 7:
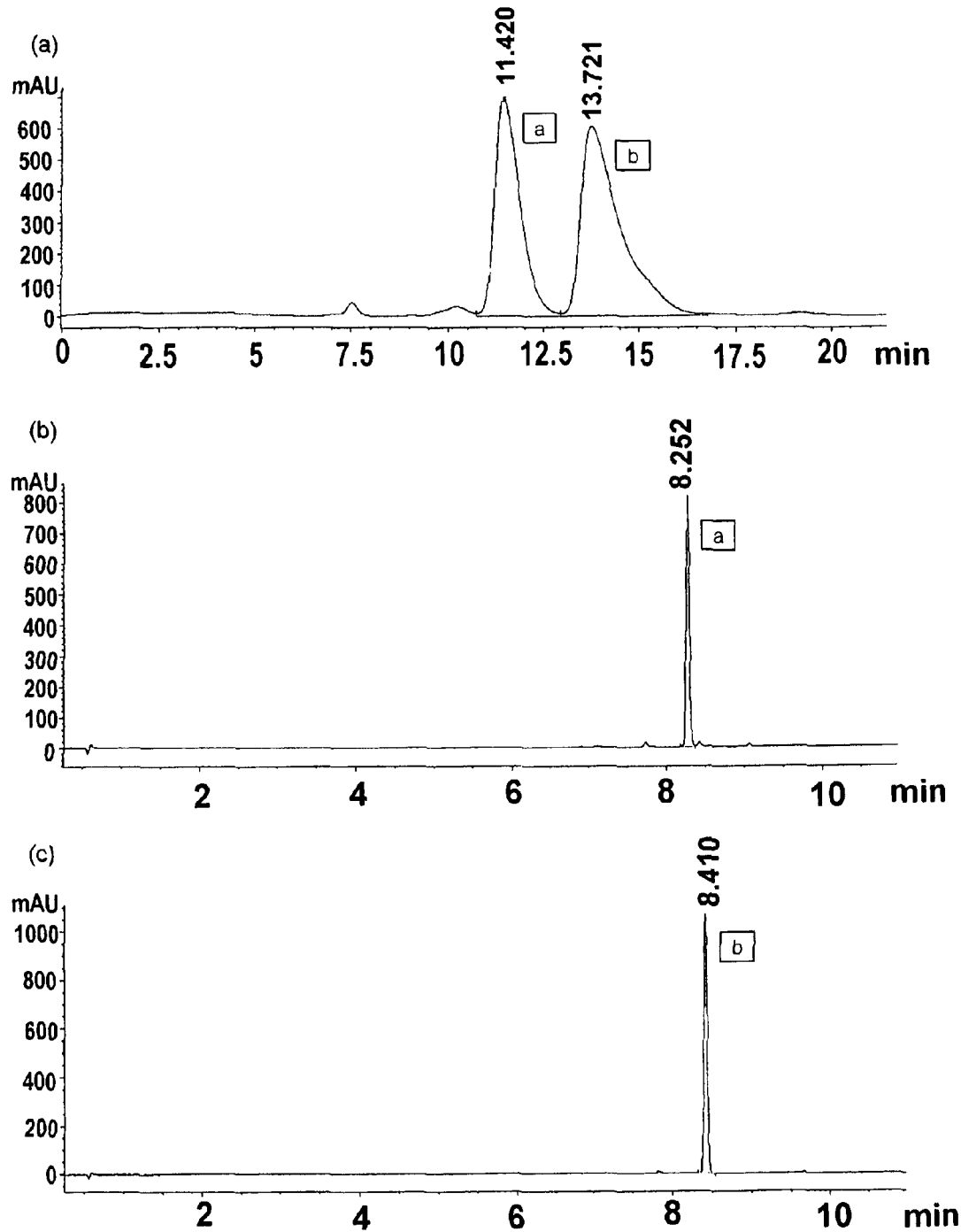
FIGS. 7a-7c are chromatograms for the separation of the mixture of (2'R,3'S)-2'-Ac-7,10-di-Troc-docetaxel (IVa) with (2'S,3'S)-2'-Ac-7,10-di-Troc-docetaxel (IVb) obtained in accordance with Example 6, an analytical HPLC chromatogram of (2'R,3'S)-2'-Ac-7,10-di-Troc-docetaxel (IVa), and an analytical HPLC chromatogram of (2'S,3'S)-2'-Ac-7,10-di-Troc-docetaxel (IVb), respectively.

Step 2 of Method (2): Separation of Mixture of (2'R, 3'S)-2'-Ac-7,10-di-Troc-docetaxel (Chemical Formula IVa) and (2'S,3'S)-2'-Ac-7,10-di-Troc-docetaxel (Chemical Formula IVb) into Each Isomer The mixture obtained from Example 1 is subjected to liquid chromatography with a column (0.45×90 cm) packed with silica gel (20-100 μm) in a scale-down mode to determine the separation efficiency. A mobile phase, 0.5% methanol/99.5% dichloromethane solution, is used at a flow rate of 1.5 mL/min to equilibrate the chromatography condition, and 4 mg of the sample is dissolved into the mobile phase solvent. All of sample is loaded onto the column. While the column is eluted continuously with the mobile phase solvent, the chromatogram is obtained by using a UV detector (FIG. 7a). The peaks corresponding to each of the isomers are collected and determined by HPLC (FIGS. 7b and 7c). The process in this example is amenable to scale-up.

EXAMPLE 7

Figure 8:
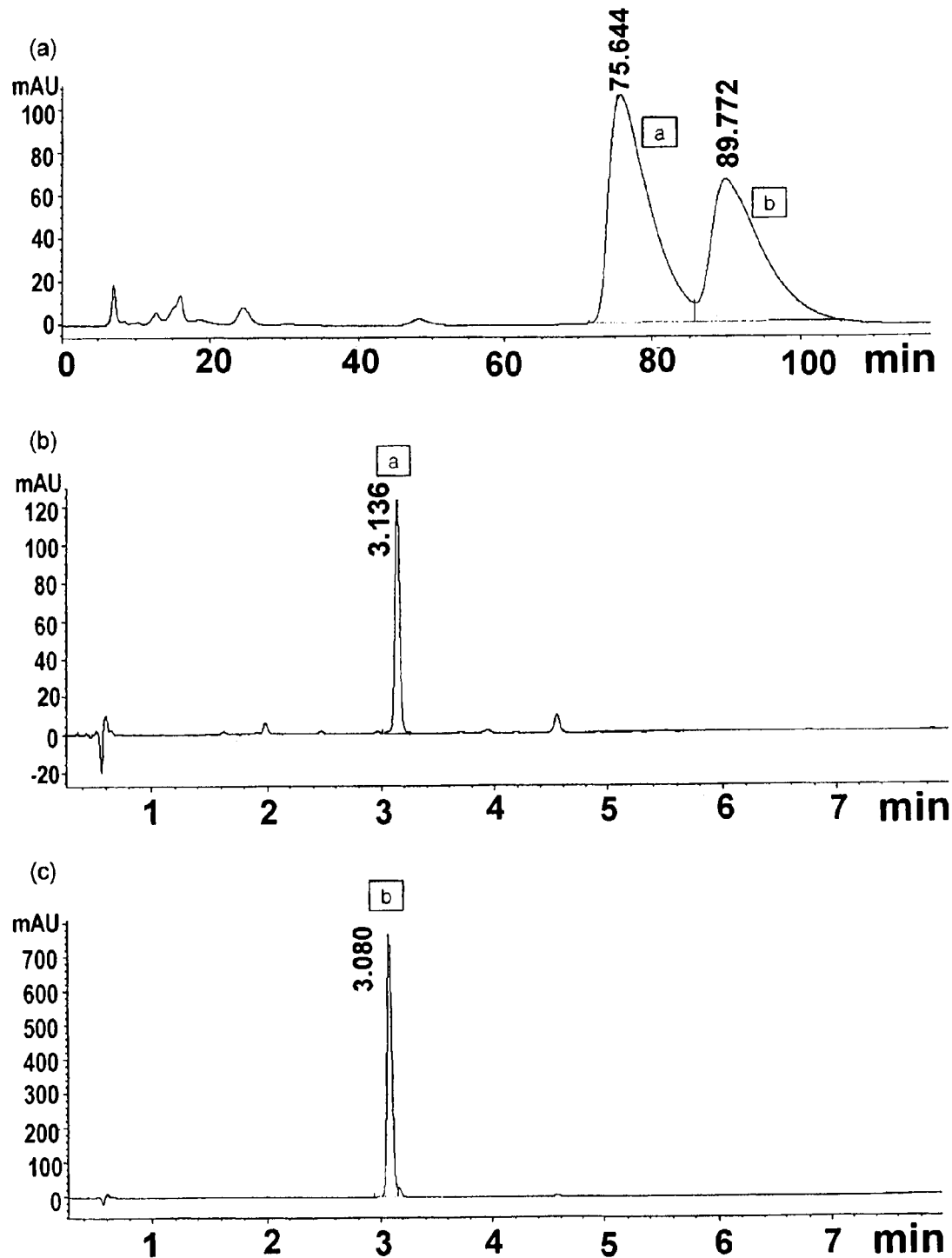
FIGS. 8a-8c are chromatograms for the separation of the mixture of (2'R,3'S)-2'-Ac-docetaxel with (2'S,3'S)-2'-Ac-docetaxel obtained in accordance with Example 7, an analytical HPLC chromatogram of (2'R,3'S)-2'-Ac-docetaxel, and an analytical HPLC chromatogram of (2'S,3'S)-2'-Ac-docetaxel, respectively.

Method (3): Separation of Mixture of (2'R,3'S)-2'-Ac-Docetaxel and (2'S,3'S)-2'-Ac-Docetaxel into Each Isomer The mixture (IVa, IVb) obtained from Example 1 is subjected to deprotection at the
Troc group in the same manner as described in Example 5 to obtain (2'R,3'S)-2'-Ac-Docetaxel (VIa) with (2'S,3'S)-2'-Ac-Docetaxel (VIb). The mixture is separated into each isomer in the same manner as described in Example 3, except that 1.5% methanol/98.5% dichloromethane is used as a mobile phase (FIG. 8a). The peak corresponding to each isomer is collected and determined by HPLC (FIGS. 8b and 8c). Each isomer separated as described above is subjected to the process as described in Example 2 to obtain (2'R,3'S)-docetaxel and (2'S,3'S)-docetaxel, from which 2'-Ac in each side chain is removed. In the compounds, (2'S,3'S)-docetaxel is reversed into (2'R,3'S)-docetaxel in the same manner as described in Example 5.

In the following Example 8, used are a side chain, i.e., a racemic mixture (mixture of Compound IIa with Compound IIb, 1:1), wherein each hydroxyl group is protected with Ac group, and 10-deacetyl-baccatin III derivative protected with Troc.

EXAMPLE 8

Figure 9:
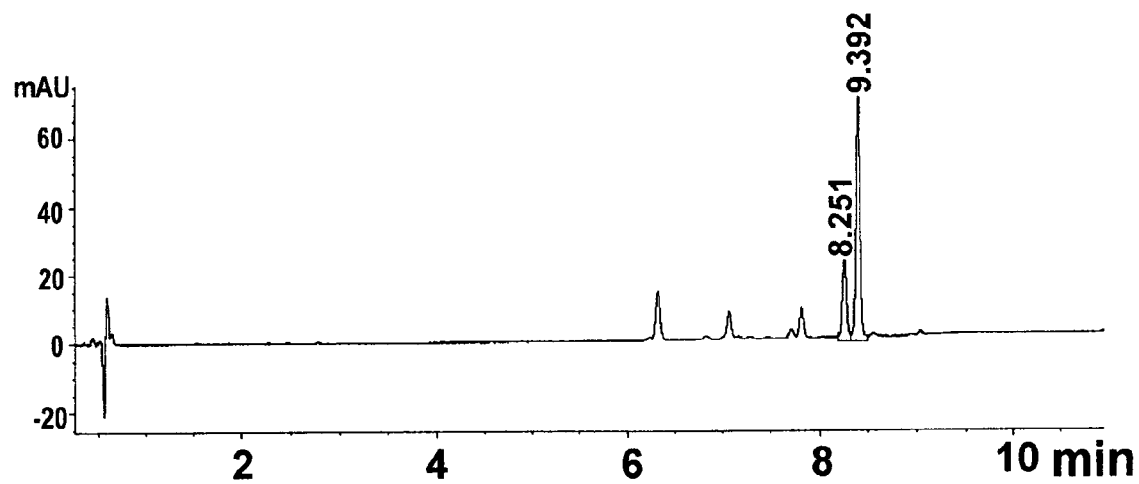
FIG. 9 is an analytical HPLC chromatogram of the mixture of (2'R,3'S)-2'-Ac-7,10-di-Troc-docetaxel with (2'S,3'S)-2'-Ac-7,10-di-Troc-docetaxel obtained in accordance with Example 8.

Step 1): Condensation of Side Chain {Mixture of (2R,3S)-2-Ac-N-Boc-3-phenylisoserine (Chemical Formula IIa) and (2S,3S)-2-Ac-N-Boc-3-phenylisoserine (Chemical Formula IIb), 1:1} with 7,10-di-Troc-10-deacetyl-baccatin III First, 1 g of 7,10-di-Troc-10-deacetyl-baccatin III (III), 0.35 g of (2R,3S)-2-Ac-N-Boc-3-phenylisoserine (IIa) and 0.35 g of (2S,3S)-2-Ac-N-Boc-3-phenylisoserine (Chemical Formula IIb) are dissolved into 10 mL of dry toluene, and an equimolar amount of DMAP is added thereto. Next, a solution of an equimolar amount of DCC dissolved in 5 mL of dry toluene is added dropwise thereto and the reaction mixture is heated to 50° C. under agitation to perform a reaction. After the completion of the reaction, 10 mL of distilled water is added to quench the reaction, and the reaction mixture is agitated for 1 hour at room temperature. Then, the reaction mixture is filtered. The filtrate is concentrated and dried, and then subjected to chromatography through a silica gel column using 5% metanol/95% dichloromethane as a mobile phase, followed by concentration and drying, to obtain 1.2 g of a mixed dry solid of (2'R,3'S)-2'-Ac-7,10-di-Troc-docetaxel and (2'S,3'S)-2'-Ac-7,10-di-Troc-docetaxel, which, in turn is determined by HPLC (see FIG. 9).

Then, the mixed dry sold is subjected to side chain deprotection, separation, a stereochemical reversion, and deprotection at 7- and 10-positions, in the same manner as described in Examples 2-5, to obtain docetaxel.

As can be seen from the above examples and accompanying drawings, it is possible to separate the intermediate, the isomer mixture, easily into each isomer merely by way of chromatographic separation. It is also possible to inject a large amount of sample onto a chromatography column. Therefore, the method in accordance with the present invention allows effective separation of isomers and efficient production of a taxane derivative even when using a significantly increased amount of a substrate. This suggests high industrial applicability of the present invention.

COMPARATIVE EXAMPLE 1

Separation of Mixture of (2'R,3'S)-docetaxel with (2'S,3'S)-docetaxel into Each Isomer In a known manner, Examples 1, 2 and 5 are repeated to obtain a product, which, in turn, is subjected to chromatographic separation in the manner as described hereinafter. Then the separation efficiency is compared with the separation efficiency obtained from the above examples.

Figure 10:
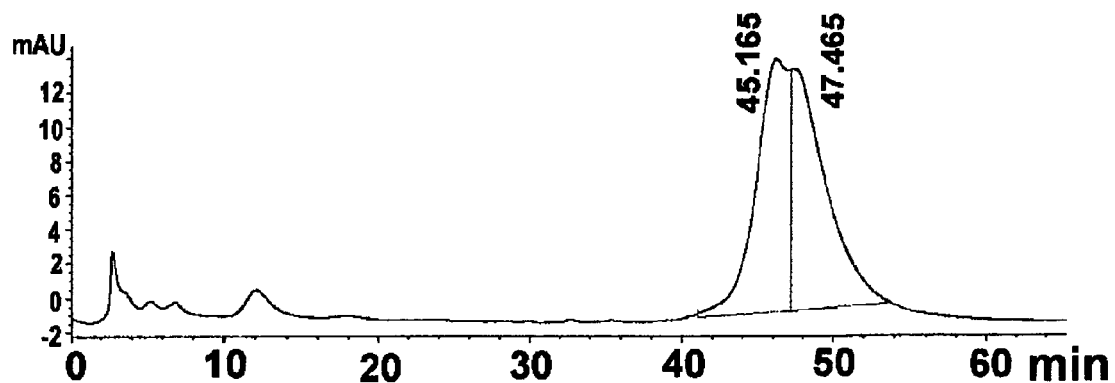
FIG. 10 is a chromatogram for the separation of the mixture of (2'R,3'S)-docetaxel with (2'S,3'S)-docetaxel as described in Comparative Example 1.

The mixed dry solid obtained from Example 2 is deprotected in the same manner as described in Example 5 to obtain a deprotected mixed dry solid. The mixed dry solid is subjected to liquid chromatography with a column (0.45×90 cm) packed with silica gel (20 μm) in a scale-down mode. A mobile phase, 2.0% methanol/98% dichloromethane solution, is used at a flow rate of 1.5 mL/min to equilibrate the chromatography condition, and 4 mg of the sample is dissolved into the mobile phase solvent. All of sample is loaded onto the column. While the column is eluted continuously with the mobile phase solvent, the chromatogram is obtained by using a UV detector. Then, the peaks corresponding to each of the isomers are collected and determined by HPLC (FIG. 10).

After carrying out the process of Comparative Example 1, the mixture is hardly separated even with the lapse of a longer separation time than Example 3. Therefore, separation of the mixture according to Comparative Example 1 requires expensive high performance liquid chromatography with collection of a small amount of product. As a result, the process according to Comparative Example 1 is not industrially applicable.

The invention has been described in detail with reference to example embodiments thereof. However, it will be appreciated by those skilled in the art that changes may be made in these embodiments without departing from the principles and spirit of the invention, the scope of which is defined in the accompanying claims and their equivalents.

The invention claimed is:
1. A method for preparing a taxane derivative represented by the following Chemical Formula (I), comprising the steps of:

1) carrying out condensation of a side chain with baccatin III represented by the following Chemical Formula III or 10-deacetyl-baccatin III derivative, having protective group(s) introduced to 7-hydroxyl group and/or 10-hydroxyl group, to obtain a mixture of a compound represented by the following Chemical Formula IVa with a compound represented by the following Chemical Formula IVb, wherein the side chain is selected from a (2R,3S)-phenylisoserine derivative, represented by the following Chemical Formula IIa and having protected groups introduced to 2-hydroxyl group and 3-amino group, and a mixture of the derivative with an isomer thereof, a (2S,3S)-phenylisoserine derivative, represented by the following Chemical Formula IIb;

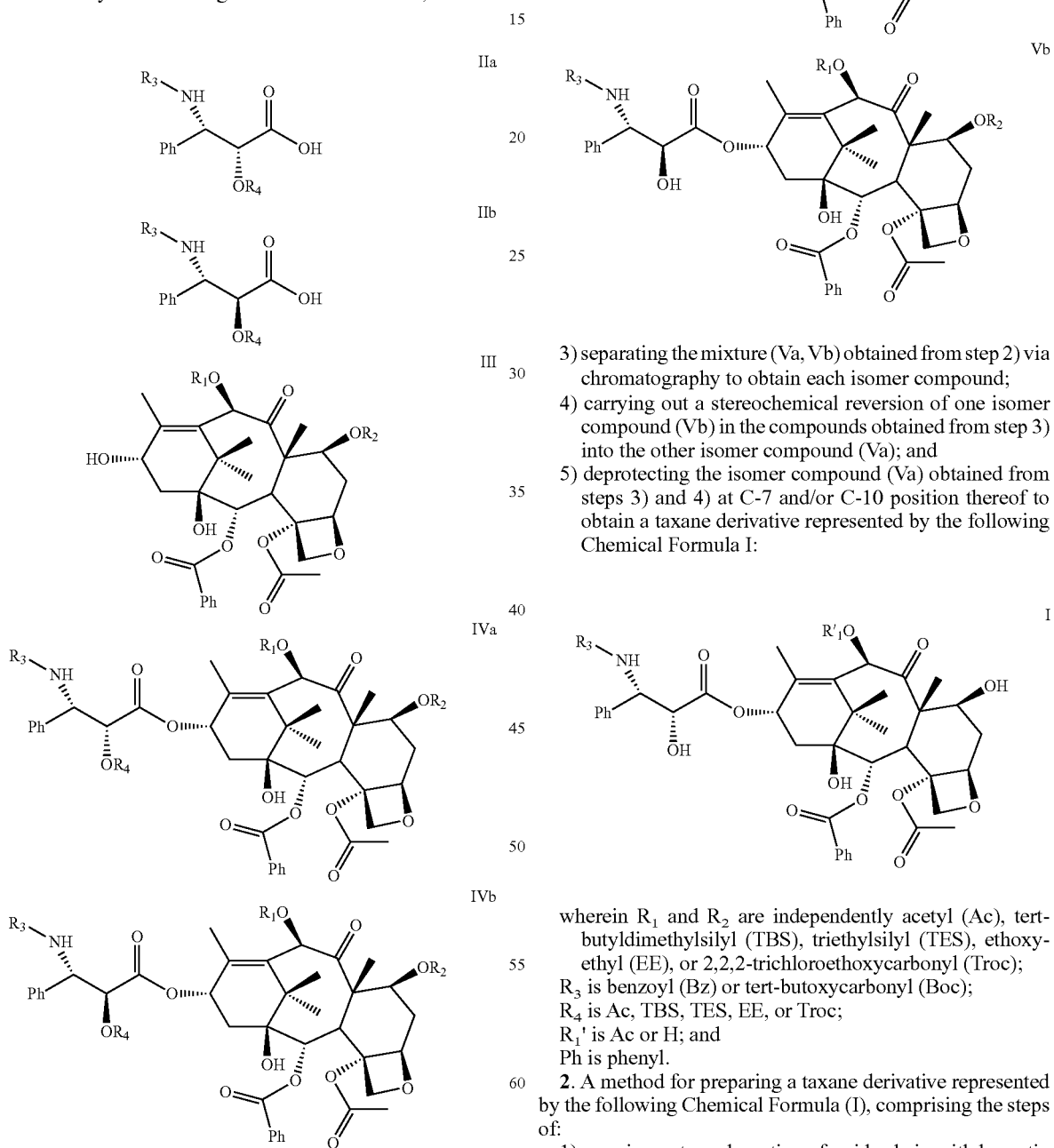

2) deprotecting the side chain of the mixture (IVa, IVb) obtained from step 1) at C-2 position thereof to obtain a mixture of a compound represented by the following Chemical Formula Va with a compound represented by the following Chemical Formula Vb;

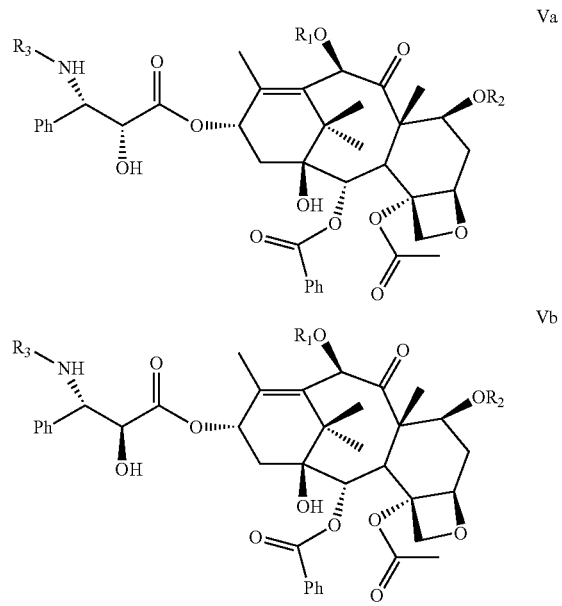

3) separating the mixture (Va, Vb) obtained from step 2) via chromatography to obtain each isomer compound;
4) carrying out a stereochemical reversion of one isomer compound (Vb) in the compounds obtained from step 3) into the other isomer compound (Va); and
5) deprotecting the isomer compound (Va) obtained from steps 3) and 4) at C-7 and/or C-10 position thereof to obtain a taxane derivative represented by the following Chemical Formula I:

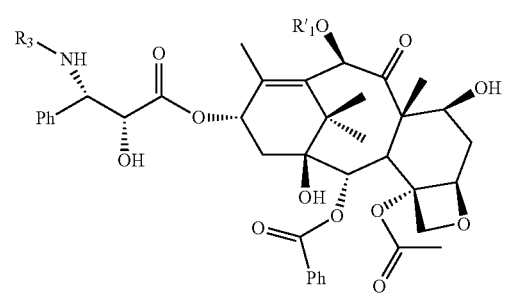

wherein $R_1$ and $R_2$ are independently acetyl (Ac), tert-butyldimethylsilyl (TBS), triethylsilyl (TES), ethoxyethyl (EE), or 2,2,2-trichloroethoxycarbonyl (Troc);
$R_3$ is benzoyl (Bz) or tert-butoxycarbonyl (Boc);
$R_4$ is Ac, TBS, TES, EE, or Troc;
$R_1'$ is Ac or H; and
Ph is phenyl.

2. A method for preparing a taxane derivative represented by the following Chemical Formula (I), comprising the steps of:
1) carrying out condensation of a side chain with baccatin III represented by Chemical Formula III or 10-deacetyl-baccatin III derivative, having protective group(s) introduced to 7-hydroxyl group and/or 10-hydroxyl group, to obtain a mixture of a compound represented by Chemical Formula IVa with a compound represented by Chemical Formula IVb, wherein the side chain is selected from a (2R,3S)-phenylisoserine derivative, represented by Chemical Formula IIa and having protected groups introduced to 2-hydroxyl group and 3-amino group, and a mixture of the derivative with an isomer thereof, a (2S,3S)-phenylisoserine derivative, represented by Chemical Formula IIb;

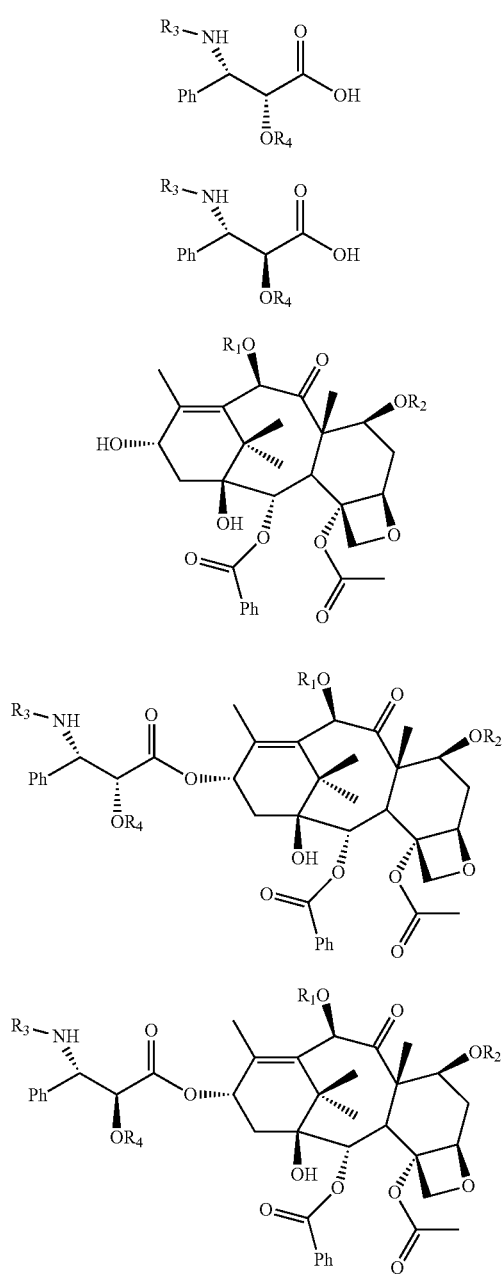

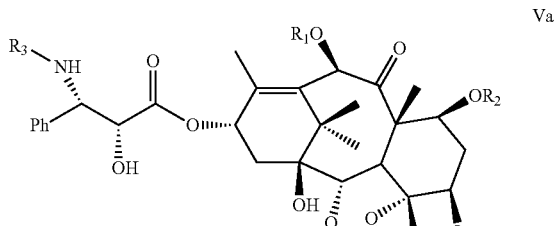

2) separating the mixture (IVa, IVb) obtained from step 1) via chromatography to obtain each isomer compound;

3) deprotecting the side chain of each isomer compound obtained from step 2) at C-2 position thereof to obtain a compound represented by Chemical Formula Va and a compound represented by Chemical Formula Vb;

4) carrying out a stereochemical reversion of one isomer compound (Vb) in the compounds obtained from step 3) into the other isomer compound (Va); and 5) deprotecting the isomer compound (Va) obtained from steps 3) and 4) at C-7 and/or C-10 position thereof to obtain a taxane derivative represented by Chemical Formula I:

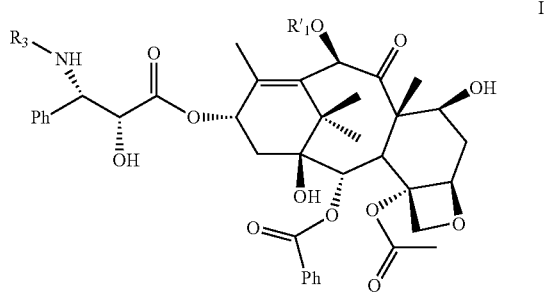

wherein $R_1$, $R_2$, $R_3$, $R_4$, $R_1'$ and Ph are the same as defined in claim 1.

3. A method for preparing a taxane derivative represented by the following Chemical Formula (I), comprising the steps of:

1) carrying out condensation of a side chain with baccatin III represented by Chemical Formula III or 10-deacetylbaccatin III derivative, having protective group(s) introduced to 7-hydroxyl group and/or 10-hydroxyl group, to obtain a mixture of a compound represented by Chemical Formula IVa with a compound represented by Chemical Formula IVb, wherein the side chain is selected from a (2R,3S)-phenylisoserine derivative, represented by Chemical Formula IIa and having protected groups introduced to 2-hydroxyl group and 3-amino group, and a mixture of the derivative with an isomer thereof, a (2S,3S)-phenylisoserine derivative, represented by Chemical Formula IIb;

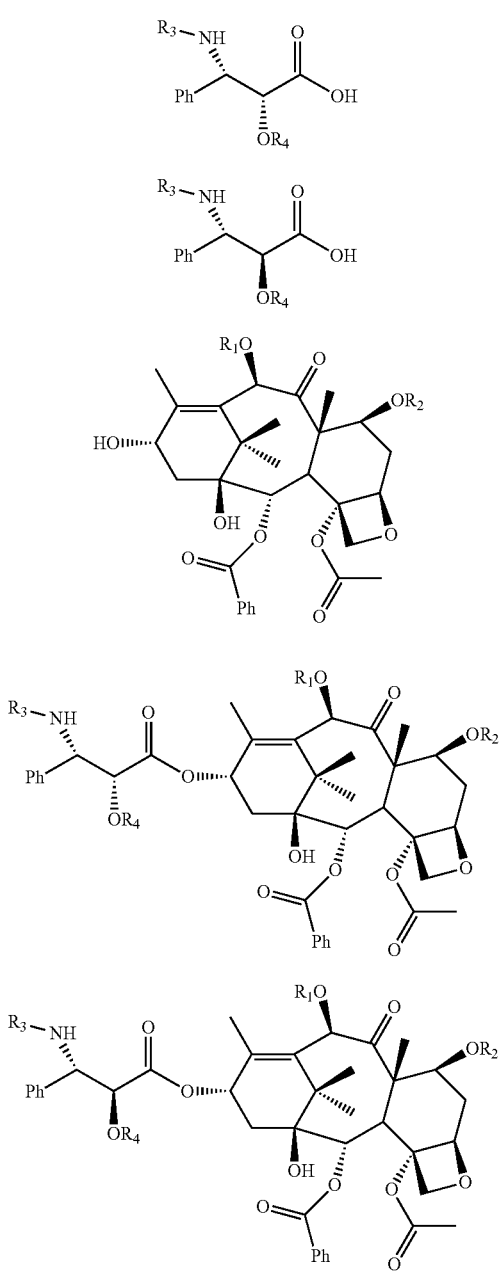

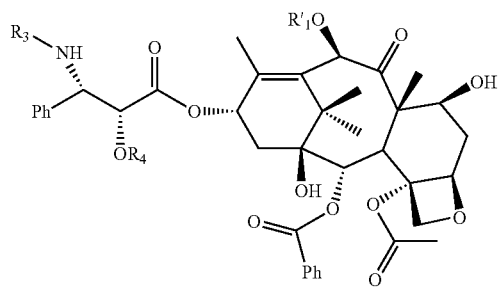

2) deprotecting the mixture (IVa, IVb) obtained from step 1) at C-7 and/or C-10 position thereof to obtain a mixture of a compound represented by the following Chemical Formula VIa with a compound represented by the following Chemical Formula VIb;

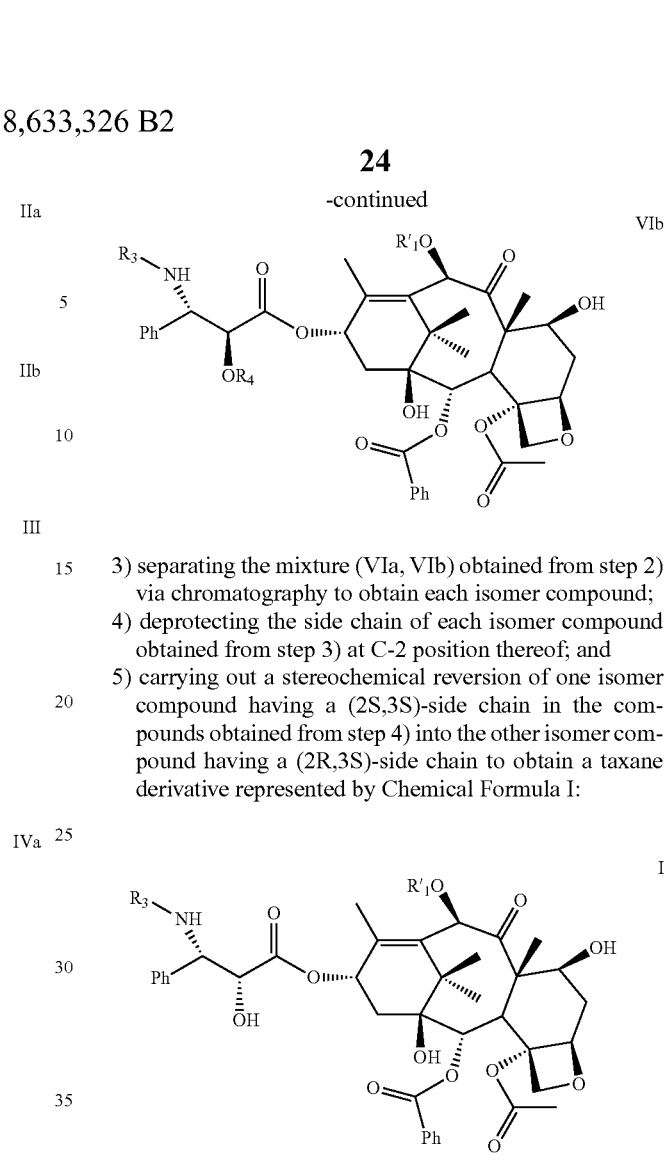

3) separating the mixture (VIa, VIb) obtained from step 2) via chromatography to obtain each isomer compound;
4) deprotecting the side chain of each isomer compound obtained from step 3) at C-2 position thereof; and
5) carrying out a stereochemical reversion of one isomer compound having a (2S,3S)-side chain in the compounds obtained from step 4) into the other isomer compound having a (2R,3S)-side chain to obtain a taxane derivative represented by Chemical Formula I:

wherein $R_1$, $R_2$, $R_3$, $R_4$, $R_1'$ and Ph are the same as defined in claim 1.

4. The method for preparing a taxane derivative according to claim 1, wherein the side chain in step 1) is a racemic mixture of (2R,3S)-phenylisoserine derivative (IIa) with (2S,3S)-phenylisoserine derivative (IIb).

5. The method for preparing a taxane derivative according to claim 1, wherein the chromatography is carried out in a normal phase chromatography mode using a column packed with silica gel having a particle diameter of 5-120 micrometers (μm).

6. The method for preparing a taxane derivative according to claim 1, wherein the stereochemical reversion is carried out by reacting the mixture of isomers with triphenylphosphine and diethylazodicarboxylate or di-tert-butylazodicarboxylate in the presence of an organic solvent.

7. The method for preparing a taxane derivative according to claim 1, wherein the taxane derivative is docetaxel or paclitaxel.

8. The method for preparing a taxane derivative according to claim 2, wherein the side chain in step 1) is a racemic mixture of (2R,3S)-phenylisoserine derivative (IIa) with (2 S,3S)-phenylisoserine derivative (IIb).

9. The method for preparing a taxane derivative according to claim 2, wherein the chromatography is carried out in a normal phase chromatography mode using a column packed with silica gel having a particle diameter of 5-120 micrometers (μm).

10. The method for preparing a taxane derivative according to claim 2, wherein the stereochemical reversion is carried out by reacting the mixture of isomers with triphenylphosphine and diethylazodicarboxylate or di-tert-butylazodicarboxylate in the presence of an organic solvent.

11. The method for preparing a taxane derivative according to claim 2, wherein the taxane derivative is docetaxel or paclitaxel.

12. The method for preparing a taxane derivative according to claim 3, wherein the side chain in step 1) is a racemic mixture of (2R,3S)-phenylisoserine derivative (IIa) with (2S,3S)-phenylisoserine derivative (IIb).

13. The method for preparing a taxane derivative according to claim 3, wherein the chromatography is carried out in a normal phase chromatography mode using a column packed with silica gel having a particle diameter of 5-120 micrometers (μm).

14. The method for preparing a taxane derivative according to claim 3, wherein the stereochemical reversion is carried out by reacting the mixture of isomers with triphenylphosphine and diethylazodicarboxylate or di-tert-butylazodicarboxylate in the presence of an organic solvent.

15. The method for preparing a taxane derivative according to claim 3, wherein the taxane derivative is docetaxel or paclitaxel.

* * * * *